United States Patent [19]

Sears

[11] 4,320,121

[45] * Mar. 16, 1982

[54] METHOD OF EMULSIFYING CHOLESTEROL, CHOLESTEROL ESTERS AND TRIGLYCERIDE COMPOUNDS

[76] Inventor: Barry D. Sears, 5 Cleveland Rd., Marblehead, Mass. 01945

[*] Notice: The portion of the term of this patent subsequent to Apr. 25, 1995, has been disclaimed.

[21] Appl. No.: 90,994

[22] Filed: Nov. 5, 1979

Related U.S. Application Data

[63] Continuation of Ser. No. 878,521, Feb. 17, 1978, abandoned, which is a continuation of Ser. No. 731,132, Oct. 12, 1976, Pat. No. 4,086,257, Ser. No. 770,290, Feb. 22, 1977, Pat. No. 4,097,503, Ser. No. 770,407, Feb. 22, 1977, Pat. No. 4,097,502, and Ser. No. 807,373, Jun. 17, 1977, Pat. No. 4,145,410.

[51] Int. Cl.$^3$ .................... A61K 31/685; C07F 9/02; C07F 9/10
[52] U.S. Cl. .................... 424/199; 424/361; 260/403; 252/316
[58] Field of Search .............. 424/199, 361; 260/403; 252/316

[56] References Cited

U.S. PATENT DOCUMENTS 2,853,419 9/1958 Degkwitz .......................... 424/361
4,159,988 7/1979 Eibl et al. .......................... 260/403

OTHER PUBLICATIONS

The New England Journal of Medicine, Sep. 1976, pp. 704–710.
Aneja et al., Biochemica et Biophysica Acta.

*Primary Examiner*—Donald B. Moyer
*Attorney, Agent, or Firm*—Richard P. Crowley

[57] ABSTRACT

A method of emulsifying water insoluble compounds particularly cholesterol, cholesterol esters and triglycerides in the blood which method comprises emulsifying the water insoluble compound with a novel synthetic phosphatidyl quaternary ammonium, sulfonium and phosphonium hydroxide compounds or emulsifying agents which compounds have a hydrophobic/hydrophilic balance different from the natural phosphatidylcholine, by changes in the polar group.

15 Claims, No Drawings

METHOD OF EMULSIFYING CHOLESTEROL, CHOLESTEROL ESTERS AND TRIGLYCERIDE COMPOUNDS

REFERENCE TO PRIOR APPLICATIONS

This is a X continuation of application Ser. No. 878,521, filed Feb. 17, 1978, now abandoned, which in turn is a continuation or part of U.S. patent applications, U.S. Ser. No. 731,132 filed Oct. 12, 1976, now U.S. Pat. No. 4,086,257, issued Apr. 25, 1978; U.S. Ser. No. 770,290 filed Feb. 22, 1977, now U.S. pat. No. 4,097,503, issued June 27, 1978; U.S. Ser. No. 770,407 filed Feb. 22, 1977, now U.S. Pat. No. 4,097,502, issued June 27, 1978; and U.S. Ser. No. 807,373 filed June 17, 1977, now U.S. Pat. No. 4,145,410, issued Mar. 20, 1979, all duly incorporated by reference in this Application.

BACKGROUND OF THE INVENTION

This invention relates to novel chemical compounds structurally related to phosphatidylcholine, to a method of preparing such compounds, and to the use as surfactants of such chemical compounds with or for compounds which have limited or no solubility in aqueous solutions.

Phospholipids and phosphatidylcholine in particular are amipathic compounds in that they consist of hydrophobic and hydrophilic groups or regions within the same molecule. Compounds with this amipathic property tend to self-associate in aqueous systems to form micelles which have a hydrophobic interior and a hydrophilic exterior. As a result, these compounds act as surfactants and can solubilize other relatively aqueous insoluble compounds which have limited or no solubility in water, and can partition such insoluble compounds into the hydrophobic region of the micelle. The external polar hydrophilic region of the micelle confers water solubility on the micelle complex or group. It has been well known that such nonsoluble biological compounds, such as cholesterol, cholesterol esters and derivatives, triglycerides and other compounds, can be solubilized in phospholipid micelles. However, the extent of solubilizing power of any surfactant is highly dependent on the ratio of hydrophobic-to-hydrophilic balance within the particular molecule.

For example, natural phosphatidylcholine (that is, lecithin) is an excellent emulsifying agent for a number of insoluble biological compounds, such as cholesterol, cholesterol esters and triglycerides, and lecithin is widely used in many industrial applications; for example, the food industry. Lecithin is a natural surfactant, and, like other such surfactants, its solubilization properties are derived from its amipathic character; that is, the molecule possesses a region of hydrophobic character (the hererogeneous fatty-acid chain) and a region of hydrophilic character (the polar head group—ethyl-N-trimethyl ammonium group). In addition, lecithin is zwitterionic in the pH range of 2-12, because it possesses a positively charged group (the quaternary ammonium group) and a negatively charged group (the phosphate group). This zwitterionic character stabilizes the ionic structure of the lecithin against any pH fluctuations that would tend to flocculate other natural detergents; that is, other phospholipids or bile salts.

The natural-occurring phospholipids are limited in solubilizing properties. For example, it is known that the maximum amount of cholesterol that phosphatidylcholine can solubilize is in a molar ratio of about one to one, while little, if any, cholesterol ester can be solubilized by phosphatidylcholine. Thus, novel phospholipid compounds which have modified solubilized properties (particularly those which solubilize a greater amount of both biological and industrial compounds than is possible with the natural compound or have different solubilized properties) would be most desirable and useful.

SUMMARY OF THE INVENTION

My invention relates to novel, synthetic, phosphatidyl compounds, particularly quaternary ammonium, phosphonium and sulfonium hydroxide compounds, which are characterized by enhanced or different solubilizing, surfactant and other properties from the heterogeneous, natural-occurring phosphatidylcholine, to the method of preparing such compounds and to the method of using such compounds as surfactants to solubilize and emulsify other compounds, particularly cholesterol and cholesterol-derived compounds and triglyceride compounds.

I have discovered in particular that the solubilizing or surfactant properties of my novel phosphatidyl compounds can be obtained by variation in the separation of the positively and negatively charged groups; that is, by increasing or decreasing the distance between the groups, such as by increasing the length of the divalent separating radical; for example, the length of the methylene radical, between the charged moieties and/or by delocation of the positive charge on and about the respective sulfur, phosphorous or quaternary nitrogen atom, such as by replacing one or more of the three methyl groups with other groups, such as with other alkyl groups. Thus, by taking advantage of the zswitterionic nature of natural phosphatidylcholine and changing the structure to produce novel compounds, modified and, in some cases, unexpected surfactant properties are obtained, particularly by the alteration and modification of the polar head group (the quaternary ammonium, quaternary phosphonium and ternary sulfonium) and region of the various phosphatidylcholines.

My new compounds are useful and interesting substitutes for lecithin in solubilizing nonaqueous soluble compounds. In particular, the new compounds, particularly the quaternary ammonium compounds, are useful in the regression of atherosclerotic lesions and as antiatherosclerotic agents in blood or other biological fluids, and as stabilizing agents and emulsifiers, particularly in food products. The compounds may be employed to emulsify other compounds, such as drugs for oral administration by a patient. Where employed as antiatherosclerotic agents, the compounds may be used as active ingredients in time-controlled capsules or tablets for oral administration or injected directly into the patient or as a pharmaceutical inert carrier liquid, either as a solution or suspension.

The novel synthetic phosphatidyl compounds of my invention are represented by the general formula:

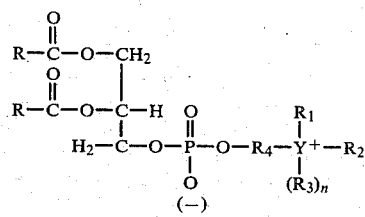

wherein $Y^+$ is a sulfur atom, a phosphorous atom or a nitrogen atom; n is a whole number of 0 or 1, and n is 1 where Y is a quaternary nitrogen or quaternary phosphorous atom, and n is 0 where Y is a ternary sulfur atom; R is a hydrocarbon radical; for example, a long-chain radical, either the same or different, straight or branch chain, and preferably a $C_{14}$ to $C_{20}$ fatty-acid/alcohol radical; $R_1$, $R_1$ and $R_3$ are hydrocarbon radicals, such as alkyl, alkylene, phenyl or alkyl-substituted phenyl radicals; for example, benzyl, and preferably are lower alkyl radicals; for example, $C_1$–$C_4$, such as methyl, ethyl, propyl, isopropyl, butyl and isobutyl radicals or a phenyl or benzyl radical, with $R_1$, $R_2$ and $R_3$ being the same or different radicals; and $R_4$ is a hydrocarbon radical, preferably a long-chain divalent hydrocarbon radical of from 1 to 10 carbon atoms; for example, 1 to 5, such as methylene radical, straight or branch chain, except for the compound where $R_1$, $R_2$ and $R_3$ are methyl and $R_4$ is a dimethylene radical. Most preferably $R_4$ is a $C_2$–$C_5$ methylene chain, and has a different number of carbon atoms than $R_1$, $R_2$ and $R_3$. The glycerol backbone of the compounds may have the d, l or racemic configuration.

The preferred phosphatidyl quaternary ammonium hydroxide compounds of my invention are represented by:

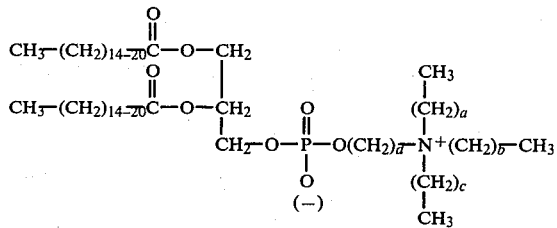

Typical compounds include:
I: a=b=o c=1 d=2
II: a=b=c=o d=4
III: a=b=c=o d=3
IV: a=b=o c=2 d=2

In my compounds, the R radicals may vary and be composed of natural or synthetic fatty radicals, but preferably are $C_{14}$ to $C_{20}$ fatty acid or alcohol radicals, or combinations and mixtures thereof. The fatty radicals useful include both saturated and ethylenically unsaturated hydrocarbon radicals, such as those radicals derived from fatty acids or alcohols, such as, for example, myristate, palmitate, oleate, linoleate and stearate radicals and heterogeneous mixtures, such as found in natural products like egg yolk, soybeans and the like.

In one method of preparation, as hereinafter described, the R radicals will be those radicals of the hydroxide or alcohol selected for the reaction. By the selection of desired fatty radicals and the length thereof, the hydrophobic character of this portion of the synthetic compound may be altered and modified to a desired defined level, such as by selecting the R radical to be the same or different chain length or degree of saturation or substitution. The polar group; for example, the quaternary ammonium, quaternary phosphonium or ternary sulfonium group of my compounds, may be composed of substituent radicals to alter the electropositive character of the positively charged atom ($Y^+$), but particularly are $C_1$–$C_4$ alkyl radicals.

My novel compounds would include, but not be limited to: dioleate phosphatidyl-(isopropyl-N-triethyl) quaternary ammonium hydroxide; dipalmitate phosphatidyl-(ethyl-N-dimethyl, ethyl) quaternary ammonium hydroxide; distearyl phosphatidyl-(ethyl-N-dimethylethyl) quaternary ammonium hydroxide; oleate-palmitate phosphatidyl-(ethyl-N-dimethylethyl) quaternary ammonium hydroxide; dimyristate phosphatidyl-(butyl-N-dipropylmethyl) quaternary ammonium hydroxide; dipalmitate phosphatidyl-(propyl-N-trimethyl) quarternary ammonium hydroxide; egg phosphatidyl-(propyl-N-trimethyl) quaternary ammonium hydroxide; soybean phosphatidyl-(propyl-N-trimethyl) quaternary ammonium hydroxide; and mixtures thereof. My novel compounds include the corresponding quaternary phosphonium compounds, as well as the ternary sulfonium compounds, such as dioleate phosphatidyl-(isopropyl-S-diethyl) sulfonium hydroxide; dipalmitate phosphatidyl-(ethyl-S-dimethyl) sulfonium hydroxide; distearyl phosphatidyl-(ethyl-S-diethyl) sulfonium hydroxide; etc.

My compounds have been described employing derived nomenclature. However, for example, dimyristate phosphatidyl-(butyl-N-dipropylmethyl) quaternary ammonium hydroxide above also may be named as dimyristoyl phosphatidyl-(tetramethylene-N-dipropylmethyl) quaternary ammonium.

My compounds may be prepared by a variety of methods. However, the preferred method of preparation is to prepare the synthetic phosphatidyl alkyl $Y^+$ hydroxide by reacting and coupling the polar head group moiety to phosphatidic acid; for example, using triisopropylbenzenesulfonyl chloride in pyridine (see R. Anjea and J. S. Chandra, Biochem. Biophys. Acta 248, 455 (1971) and B. Sears, W. C. Hutton, and T. E. Thompson, Biochem, Biophys, Res. Comm. 60, 1141 (1974)). The phosphatidic acid may be derived from natural or synthetic phosphatidylcholine by the digestion with the enzyme phospholipase D (see R. M. C. Dawson, Biochem. J. 102, 76 (1967)). The modified polar head group compound is then synthesized by the general reaction method represented and illustrated by the use of the quaternary ammonium alcohol as follows:

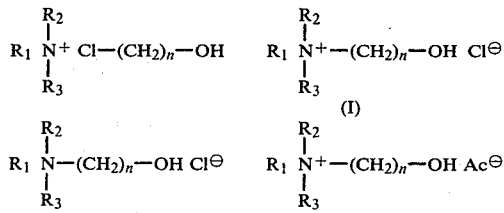

The salt form; for example, the acetate form of the salt, is obtained by ion-exchanging the halide salt; for example, the chloride form, in an ion-exchange column equilibrated with the acetate ions. Thus, my method comprises: synthesizing synthetic phosphatidylcholine or isolating natural phosphatidylcholine; then enzymatically cleaving the phosphatidylcholine to phosphatidic acid; synthesizing a modified hydroxy quaternary alkyl ammonium halide; converting the quaternary hydroxy alkyl ammonium halide to the corresponding acetate (the acetate form being more soluble than the halide from in pyridine, the solvent used for coupling), and covalently coupling with quaternary alkyl ammonium acetate onto the phosphatidic acid, thereby giving my synthetic phospholipid modified in the polar head group. The acetate or weak-acid form may also be used with acetonitrile as the solvent or the iodide form used where the coupling solvent is about a 1:1 mixture of pyridine and acetonitrile.

My method of preparing synthetic phosphatidyl compounds comprises covalently reacting or coupling in a common nonaqueous solvent, typically an organic polar solvent like pyridine or acetonitrile; for example, a nitrogen-containing solvent, the $Y^+$ salt, preferably the weak acid salt or halo salt of the $Y^+$ compound, with phosphatidic acid and recovering the phosphatidyl alkyl quaternary hydroxide compound and chromatographically purifying the resulting compound.

My invention will be described for the purpose of explanation and illustration only in connection with the preparation of certain preferred compounds. However, it is recognized and is within the scope and intent of my invention and disclosure that other compounds and other methods of preparation can be formulated and used.

DESCRIPTION OF THE EMBODIMENTS

Synthesis of dipalmitoyl phosphatidyl ammonium hydroxide compounds

Glycerol phosphoryl choline was derived from crude egg yolk phosphatidylcholine using the method of J. S. Chandra, Chem. Phys. Lipids 4 104 (1970). Dipalmitoyl phosphatidylcholine was synthesized according to the method of Cubero Robles, E. and van de Berg, D., Biochem. Biophys. Acta 187 520 (1969). Dipalmitoyl phosphatidic acid was prepared by the enzymatic cleavage of dipalmitoyl phosphatidylcholine by cabbage phospholipase D according to Dawson, R. M. C., Biochem. J. 102 76 (1967). The appropriate hydroxy alkyl ammonium acetate was covalently linked to the dipalmitoyl phosphatidic acid using 2,4,6-triisopropylbenzenesulfonyl chloride as a coupling agent as described by Sears et al, Biochem. Biophys. Res. Comm. 60 1141 (1974). The phosphatidylcholine analog was then purified by silicic acid chromatography. The detailed synthetic description of the hydroxyl alkyl ammonium compounds and the corresponding phosphatidylcholine compounds is described below.

A. Dipalmitoyl phosphatidyl-(ethyl-N dimethyl, ethyl) ammonium hydroxide (I).

0.975 g (10.9 millimoles) of dimethyl ethanolamine was placed in a 50-ml round-bottom flask. The flask was cooled to $-10°$ C. and 1.159 g (7.43 millimoles) of ethyl iodine was added with stirring. The reaction mixture was allowed to warm slowly to room temperature and was then kept in the dark for 72 hours. At the end of 72 hours, the mixture was dissolved in 20 ml of 2 M $NH_4OH$. The solution was applied to a $2 \times 40$ cm column of Bio Rad 50W-$\times 8$ cationexchange resin. The column was washed with 500 ml of 2 M $NH_4OH$. The (2-hydroxy ethyl)N-dimethyl, ethyl ammonium cation was released from the column by the addition of 300 ml of 0.5 M $NH_4HCO_3$. The (2-hydroxy ethyl)N-dimethyl-ethyl ammonium bicarbonate solution was evaporated to dryness and then taken up in distilled water. The solution was placed on a $2 \times 40$ cm column of Bio Rad AG1-$\times 8$ cationexchange column in the acetate form. The column was eluted with distilled water. The (2-hydroxy ethyl)N-dimethyl-ethyl ammonium acetate was concentrated by dryness. Thin-layer chromatography in an isopropyl alcohol/water/14 M $NH_4OH$ (7:2:1) system gave only a single spot upon iodine staining. Colormetric analysis for quaternary ammonium salts gave an overall yield of 70% (7.7 millimoles). 375 micromoles of the (2-hydroxy ethyl)N-dimethyl-ethyl ammonium acetate in methanol was mixed with 275 micromoles of dipalmitoyl phosphatidic acid and then taken to dryness. The mixture was dried under high vacuum against $P_2O_5$ overnight. 760 micromoles of 2,4,6 triisopropylbenzenesulfonyl chloride in 5 ml of dry pyridine was added to the dry mixture. The reaction mixture was stoppered and heated and stirred for 1 hour at 65° C. and then stirred for 4 hours at room temperature. At the end of the reaction, the pyridine was evaporated from the reaction. The residue was taken up in 20 ml of chloroform-methanol (2:1) and then 5 ml of distilled water was added. The resulting lower phase was taken to dryness and the residue was taken up in chloroform. The chloroform solution was applied to $2 \times 30$ cm silicic acid column and the phosphatidylcholine eluted with increasing amount of methanol in chloroform. The phosphatidylcholine gave only a single spot by thin-layer chromatography. The yield based on colormetric phosphorous analysis was 17% (46.6 micromole). The elemental analysis gave the following results:

Theoretical: C 64.31, H 10.98, N 1.83, P 4.05. Experimental: C 64.12, H 11.14, N 1.66, P 3.93.

B. Dipalmitoyl phosphatidyl-(butyl-N-trimethyl) ammonium hydroxide.

1.0 g (11.2 millimole) of 4-amino butanol was placed in a 50-ml flask and precooled to $-10°$ C. 1.6 g (11.3 millimoles) of methyl iodine was added with stirring. The reaction mixture was allowed to warm to room temperature and was kept for 72 hours in the dark. The reaction mixture was purified as described for the (2-hydroxyl ethyl)-N dimethyl ethyl ammonium acetate. The final yield of (4-hydroxy butyl)-trimethyl ammonium acetate was 17% (1.8 millimoles). 750 micromoles of (4-hydroxy butyl)-trimethyl ammonium acetate and 500 micromoles of dipalmitoyl phosphatidic acid were mixed in methanol and taken to dryness. The mixture was dried under high vacuum against $P_2O_5$ overnight. 1250 micromoles of 2,4,6 triisopropylbenzenesulfonyl chloride in 10 ml of pyridine was added. The reaction was heated for 1 hour at 65° C. and then stirred for 4 hours at room temperature. The reaction was then purified as described above. The final yield of dipalmitoyl phosphatidyl-(butyl, N-trimethyl) ammonium hydroxide was 9.7% (48 micromoles) based on phosphorous analysis. Only a single spot was observed by thin-layer chromatography.

Elemental analysis Theoretical C 64.69, H 11.0, N 1.79, P 3.98. Experimental C 64.93, H 10.72, N 1.70, P 4.12.

C. Dipalmitoyl phosphatidyl-(propyl-N-trimethyl) ammonium hydroxide.

2 g (26.6 millimoles) of 3-amino propanol was placed in a 50-ml round-bottom flask and cooled to $-10°$ C. 3.78 g (26.6 millimoles) of methyl iodine was added with stirring. The stoppered reaction mixture was allowed to warm to room temperature. This flask was kept in the dark for 48 hours. The (3-hydroxy propyl)-trimethyl ammonium salt was purified and converted to the acetate salt as previously described. Only a single spot was seen by thin-layer chromatography. The yield by colormetric analysis was 21% (5.5 millimoles). 367 micromoles of (3-hydroxy propyl)-trimethyl ammonium acetate and 245 micromoles of dipalmitoyl phosphatidic acid were mixed in methanol and evaporated to dryness. The residue was dried at high vacuum and against P$_2$O$_5$ for 12 hours. 612 micromoles of 2,4,6 triisopropylbenzenesulfonyl chloride in 5 ml of pyridine was added. The reaction was heated at 65° C. for 1 hour and then stirred for 4 hours at room temperature. The dipalmitoyl phosphatidyl(propyl-N-tri-methyl ammonium hydroxide was purified as previously described. Only a single spot was seen by thin-layer chromatography.

The elemental analysis was as follows: Theoretical: C 64.48, H 10.92, N 1.70, P 3.88. Experimental: C 64.31, H 10.98, N 1.83, P 4.05.

D. Dipalmitoyl phosphatidyl-(ethyl-N-dimethyl, propyl) ammonium hyroxide.

0.975 g (10.9 millimoles) of dimethyl ethanolamine was placed in a 50-ml round-bottom flask and cooled to −10° C. 5.61 g (33 millimoles) of propyl iodine was added with stirring. The mixture was allowed to warm to room temperature and was then kept in the dark for 72 hours. The (2-hydroxy) N-dimethyl, propyl ammonium acetate was purified as previously described. 750 micromoles of (2-hydroxy)N-dimethyl, propyl ammonium acetate and 500 micromoles of dipalmitoyl phosphatidic acid were mixed in methanol and taken to dryness. The residue was dried under high vacuum and against P$_2$O$_5$ overnight. 1250 micromoles of 2,4,6 triisopropylbenzenesulfonyl chloride in 15 ml of pyridine was added to the residue. The mixture was heated for 1 hour at 65° C. and then stirred for 4 hours at room temperature. The purification of the dipalmitoyl phosphatidyl-(ethyl-N-dimethyl propyl) ammonium hydroxide was carried out as previously described. Thin-layer chromatography showed only a single spot.

The elemental analysis gave the following: Theoretical: C 64.69, H 11.00, N 1.79, P 3.98. Experimental: C 65.16, H 11.74, N 1.78, P 3.96.

I have described the synthesis of a selected number of preferred phosphatidylcholine compounds in which the hydrophilic region of the molecule has been chemically modified. As a result, the hydrophobic-to-hydrophilic balance within the molecule is altered. One criterion of this alteration is the relative mobility of these new compounds on silicic-acid, thin-layer chromatograms. The mobility of the compound is directly related to the molecular structure of the molecule.

By changing the hydrophilic region of the phosphatidylcholine molecule, all of the described compounds now have different migration rates. Three of the compounds (A, B, D) have mobilities greater than the phosphatidyl, whereas one (C) has a mobility less than phosphatidylcholine. Therefore, the hydrophobic-to-hydrophilic balance in each of the phosphatidylcholine molecules has been altered.

Synthesis of dipalmitoyl phosphatidyl phosphonium hydroxide compounds

Glycerol phosphoryl choline is derived from crude egg yolk phosphatidylcholine using the method of J. S. Chandra, Chem. Phys. Lipids 4 104 (1970). Dipalmitoyl phosphatidylcholine is synthesized according to the method of Cubero Robles, E. and van de Berg, D., Biochem. Biophys. Acta 187 520 (1969). Dipalmitoyl phosphatidic acid is prepared by the enzymatic cleavage of dipalmitoyl phosphatidylcholine by cabbage phospholipase D according to Dawson, R. M. C., Biochem. J. 102 76 (1967). The appropriate hydroxy alkyl phosphonium acetate is covalently linked to the dipalmitoyl phosphatidic acid using 2,4,6 triisopropylbenzenesulfonyl chloride as a coupling agent as described by Sears et al, Biochem. Biophys. Res. Comm. 60 1141 (1974). The phosphatidylcholine analog is then purified by silicic acid chromatography. The detailed synthetic description of the hydroxy alkyl phosphonium compounds and the corresponding phosphatidylcholine compounds is described below.

A. Dipalmitoyl phosphatidyl-(butyl-P-trimethyl) phosphonium hydroxide.

0.4 moles of trimethyl phosphine and 0.5 moles of 4-chloro-butanol are dissolved in 200 ml of ether and allowed to sit for 24 hours at room temperature in the dark. The precipitated 4-hydroxy ethyl-P-(trimethyl) phosphonium chloride is filtered off and then dissolved in 50 ml of water. The reaction mixture is purified as described for the (2-hydroxy ethyl)-P-triethyl phosphonium acetate. 500 micromoles of (4-hydroxy butyl)-P-trimethyl phosphonium acetate and 300 micromoles of dipalmitoyl phosphatidic acid are mixed in methanol and taken to dryness. The mixture is dried under high vacuum against P$_2$O$_5$ overnight. 800 micromoles of 2,4,6 triisopropylbenzenesulfonyl chloride in 10 ml of pyridine is added. The reaction is heated for 1 hour at 65° C. and then stirred for 4 hours at room temperature. The reaction is then purified. The chloroform solution is applied to 2×30 cm silicic acid column and the phospholipid eluted with increasing amounts of methanol in chloroform. Other phosphonium compounds of my invention are prepared in a similar manner.

Synthesis of dipalmitoyl phosphatidyl sulfonium hydroxide compounds

Glycerol phosphoryl choline is derived from crude egg yolk phosphatidylcholine using the method of J. S. Chandra, Chem. Phys. Lipids 4 104 (1970). Dipalmitoyl phosphatidylcholine is synthesized according to the method of Cubero Robles, E. and van de Berg, D., Biochem. Biophys. Acta 187 520 (1969). Dipalmitoyl phosphatidic acid is prepared by the enzymatic cleavage of dipalmitoyl phosphatidylcholine by cabbage phospholipase D according to Dawson, R. M. C., Biochem. J. 102 76 (1967). The appropriate hydroxy alkyl sulfonium acetate is covalently linked to the dipalmitoyl phosphatidic acid using 2,4,6 triisopropylbenzenesulfonyl chloride as a coupling agent as described by Sears et al, Biochem. Biophys, Res. Comm. 60 1141 (1974). The phosphatidylcholine analog is then purified by silicic acid chromatography. The detailed synthetic description of the hydroxy alkyl sulfonium compounds and the corresponding phosphatidyl alkyl sulfonium hydroxide compounds are described below.

A. Dipalmitoyl phosphatidyl-(ethyl-S-dimethyl) sulfonium hydroxide (I).

Dimethyl sulfide (0.4 moles) and 2-bromo ethanol (0.3 moles) are dissolved in 50 ml of ether and allowed to sit for 24 hours in the dark at room temperature. The precipitated 2-hydroxy ethyl-S-dimethyl sulfonium bromide is filtered and then dissolved in 20 ml of water. The solution is placed on a 2×40 cm column of Bio Rad AG1-X8 cation-exchange column in the acetate form. The column is eluted with distilled water. The (2-hydroxy ethyl)S-dimethyl sulfonium acetate is concentrated by dryness. 400 micromoles of the (2-hydroxy ethyl)S-dimethyl sulfonium acetate in methanol is mixed with 300 micromoles of dipalmitoyl phosphatidic acid and then taken to dryness. The mixture is dried under high vacuum against P$_2$O$_5$ overnight. 700 micromoles of 2,4,6 triisopropylbenzenesulfonyl chloride in 10 ml of dry pyridine is added to the dry mixture. The reaction mixture is stoppered and heated and stirred for 1 hour at 65° C. and then stirred for 4 hours at room temperature. At the end of the reaction, the pyridine is evaporated from the reaction. The residue is taken up in 20 ml of chloroform-methanol (2:1) and then 5 ml of distilled water is added. The resulting lower phase is taken to dryness and the residue is taken up in chloroform. The chloroform solution is applied to 2×30 cm silicic acid column and the phosphatidyl alkyl sulfonium hydroxide eluted with increasing amounts of methanol in chloroform.

I have described the synthesis of a selected number of preferred phosphatidylcholine compounds in which the hydrophilic region of the molecule has been modified chemically. As a result, the hydrophobic-to-hydrophilic balance within the molecule is altered. Furthermore, the charge density of the positively charged phosphonium atom is significantly different from that of the quaternary ammonium atom usually found in phosphatidylcholine.

These new compounds have utility as solubilizing agents in food-processing, industrial and biological applications. In addition, becuase of their close structural relation to phosphatidylcholine, they also find application in clinical medicine, such as the regression of atherosclerotic lesions, via the solubilization of deposited cholesterol.

Amnipathic compounds because of their ability to form micelles, have the ability to solubilize compounds that are normally insoluble in water. The water insoluble compounds can be sequestered in the hydrophobic interior of the mixed micelle and therefore be removed from the aqueous environment.

The synthetic phosphatidyl compounds may be used to emulsify compounds which have low or little, if any, water solubility. The solubilization of such compounds, particularly biological hydrophobic compounds such as cholesterol, cholesterol esters, and triglycerides can be accomplished by mixing the water insoluble compounds with the phosphatidyl compounds in a suitable organic solvent such as a volatile solvent like or alcohol such as methanol followed by the evaporation of the solvent. Addition of water to the dried mixture will cause the formation of mixed micelles composed of the phosphatidyl compounds and the water insoluble compounds. As a result, these biological or other compounds which are normally insoluble in water, become effectively solubilized in the form of the mixed micelle. More vigorous homogenization such as by sonication or other devices can reduce the heterogenity of the mixed micelle size distribution and therefore give a more homogeneous preparation.

Another method of preparing the mixed micelles involves the injection of an organic solution containing the water insoluble compounds and the phosphatidyl compounds into an aqueous environment. If the organic solvent has water solubility such as an alcohol like ethanol or ester or ether like dioxane, then the rapid dilution of the solvent in the water will produce the mixed micelle. Alternatively, the phosphatidyl compounds and the water insoluble compounds can be dissolved in volatile solvent like ether and slowly injected into a heated aqueon solution. With the evaporation of the ether, the mixed micelle is formed.

A third method of emulsification consists of adding the synthetic phosphatidyl compounds as a dry mixture or as a micelle to an aqueous suspension of the water insoluble compounds. Upon vigorous homogenization or sonication, a mixed micellar solution results. Of the suggested methods of emulsification, this last method is the least preferred as it would give the least homogeneous size distribution of the mixed micelles.

Not only can the phosphatidyl compounds emulsify water insoluble compounds, but, in addition, such compounds have the ability to extract such water insoluble biological compounds from other micelles or membranes by an exchange mechanism. An example of this is shown in data in which is demonstrated the enhanced ability of the synthetic quaternary ammonium phosphatidyl compounds compared to lecithin to extract cholesterol from lecithin-cholesterol membranes.

In order to demonstrate that the synthetic phosphatidyl compounds have unobvious and unexpected properties compared to lecithin, methods have been devised to evaluate quantitatively the ability of the synthetic compounds and lecithin to solubilize cholesterol. The criteria of solubilization is the ability of the compounds to form micellar complexes with cholesterol that are small enough to pass through a $0.22\mu$ membrane filter. Since lecithin is a natural compound that is found in close association with cholesterol in natural mammalian membranes, it would be expected that lecithin would be able to solubilize cholesterol to a better degree than for example the synthetic phosphatidyl ammonium hydroxide compounds.

Another physical property important in the use of the synthetic compounds as solubilizing agents to solubilize cholesterol and other non aqueous compounds is the ability of the compounds to deplete cholesterol from lecithin model membranes saturated with cholesterol. Again, the predicted result would be that lecithin should not only deplete more cholesterol, but also to do it at a faster rate than the synthetic compounds.

The synthetic compounds demonstrate unexpected and superior abilities compared to the natural compounds, lecithin. This is highly unexpected and could not be predicted from the synthetic modifications made in the polar head moiety of the synthetic compounds. The synthetic compounds are decidedly superior to lecithin in its most important biological and industrial function, namely, the ability to solubilize water insoluble compounds, most notably cholesterol.

Ability of Synthetic Compounds to Solubilize Cholesterol

The ability of the compounds and lecithin to solubilize cholesterol was tested by determining how much radioactive cholesterol could interact with each phospholipid to form micelles small enough to pass through a $0.22\mu$ filter. This size discrimination was chosen since this size filter is usually used for the sterilization of biological solutions. 5.56 $\mu$mole of each phospholipid and an excess amount of $^3H$ cholesterol (6.12 $\mu$moles) were evaporated to dryness. The samples were dried against $P_2O_5$ under high vacuum overnight. A sample containing only cholesterol was also prepared similarly. 4 ml of distilled water was added to each sample and the mixture was vortexed at 40° C. for 5 minutes. Each sample was then sonicated for exactly 5 minutes at 40° C. Immediately, after sonication, 1 ml of the sample was passed through a $0.22\mu$ membrane filter. 0.5 ml of supernatant was placed in 10 ml of dioxane based liquid scintillation fluid. The radioactivity was counted in a liquid scintillation counter.

Table I shows the ability of a selection of synthetic quaternary ammonium compounds to solubilize excess amounts of cholesterol so that phospholipid-cholesterol micellar complex can pass through a 0.22μ filter. Cholesterol alone was unable to pass through the filter under the experimental conditions. Dimyristoyl lecithin was the least effective phospholipid in solubilizing cholesterol whereas dimyristoyl butyl-N-(trimethyl) ammonium hydroxide was the most effective. The relative efficiency of the synthetic compounds compared to lecithin are also determined. The synthetic compounds were from 5 to 30 times more efficient in solubilizing cholesterol than was lecithin.

TABLE I

| COMPOUND | FILTRATE (cpm)[a] | RELATIVE EFFICIENCY[b] |
|---|---|---|
| Dimystroyl lecithin | 70 | 1.0 |
| Dimystroyl phosphatidyl propyl-N-(trimethyl) ammonium hydroxide | 371 | 5.3 |
| Dimystroyl phosphatidyl-ethyl-N-(dimethyl, ethyl)[a] ammonium hydroxide | 493 | 7.0 |
| Dimystroyl phosphatidyl ethyl-N-(dimethyl, propyl) ammonium hydroxide | 924 | 13.2 |
| Dimystrol phosphatidyl butyl-N-(trimethyl) ammonium hydroxide | 2109 | 30.1 |
| Control (no phospholipid) | 0 | — |

Remarks
[a] $^3H$ cholesterol counts in the solution that passes through 0.22 μ filter.
[b] Determined by dividing $^3H$ cholesterol complexed with lecithin as compared to the other phospholipids.

Ability to Deplete Cholesterol from Lecithin-Cholesterol Micelles

The ability of the synthetic compounds and lecithin to deplete cholesterol from lecithin micelles saturated with cholesterol were tested by determining the amount of $^3H$ cholesterol that could be depleted per unit of phospholipid tested.

The depletion of $^3H$ cholesterol from preformed membranes was done as described by Rothman and Davidowicz (Biochemistry 14 2809 (1975). Lecithin (10 μmoles) and saturating amounts of $^3H$ cholesterol (10 μmoles) were evaporated to dryness and dried further against $P_2O_5$ under high vacuum. 0.5 ml of distilled water was added to the dried lipids and the mixture was vortexed for 2 minutes at 40° C. These are termed unsonicated dispersions. 20 μmole of each phospholipid and a trace amount of $^{14}C$ cholesteryl oleate were evaporated to dryness and dried against $P_2O_5$ under high vacuum. 4 ml of distilled water was added to each phospholipid sample. The mixtures were vortexed at 40° C. for 5 minutes and then sonicated for 15 minutes at 40° C. These are termed sonicated dispersions. 1.2 ml of the sonicated dispersions were spun at 10,000 G for 5 minutes to sediment any undispersed lipid. 0.9 ml of above sonicated vesicles were incubated with 0.5 ml of the unsonicated dispersions and the unsonicated dispersions. 0.5 ml of the supernant was then counted in the liquid scintillation counter. The $^3H$ counts represent the amount of cholesterol depleted from the unsonicated dispersions, and the $^{14}C$ counts represents the amount of phospholipid remaining in solution. The ratio of $^3H/^{14}C$ represents the amount of depleted cholesterol per unit of phospholipid.

As in the preceding example, dimyristoyl phosphatidyl butyl-N-(trimethyl) ammonium hydroxide was the most effective in terms of both rate of depletion and extent of depletion. Our other compounds were also superior to dimyristoyl lecithin in depleting cholesterol.

The synthetic compounds demonstrate an enhanced ability to deplete cholesterol from lecithin micelles saturated with cholesterol. The enhanced amount and kinetics of the cholesterol depletion must also be related to the altered hydrophobic to hydrophibic balance in the synthetic compounds compared to lecithin.

A use of this efficient ability to extract or emulsify cholesterol and other compounds is found in the regression of atherosclerotic lesions which are characterized by excess deposits of cholesterol and cholesterol esters. Such an ability has been demonstrated for lecithin. Based on in vitro studies, the ammonium phosphatidyl compounds should be even more effective in the removal of cholesterol and cholesterol esters from such atherolsclerotic lesions. The effectiveness of lecithin in such cholesterol removal depends on the mode of delivery. Simple oral administration has little or no effect as lecithin is enzymatically degraded before it can reach the circulatory system. Therefore, only intravenous injection of lecithin has been shown to be effective. A typical intravenous dosage for synthetic phosphatidyl compounds to remove deposited cholesterol would range from about 10 to 100 mg/kg of body weight. However, unlike lecithin, the synthetic phosphatidyl compounds are surprisingly resistant to enzymatic degradation as shown for example in pending application U.S. Ser. No. 807,373 filed June 17, 1977.

Therefore, the synthetic phosphatidyl compounds are effective when orally administered with a typical oral dosage ranging from about 100 to 1000 mg/kg of body weight. The synthetic compounds may be administered by direct injection into the blood stream or preferably by oral administration per se or in combination with other ingredients and additives such as in capsule, tablet, solution, suspension, in a pharmaceutically acceptable combination.

I claim:
1. A method of emulsifying a water-insoluble compound to form a mixed micelle product, which method comprises: admixing a water-insoluble compound, selected from the group consisting of water-insoluble compounds of cholesterol, cholesterol esters and triglycerides, with a synthetic quaternary-ammonium phosphatidyl compound having the general structural formula:

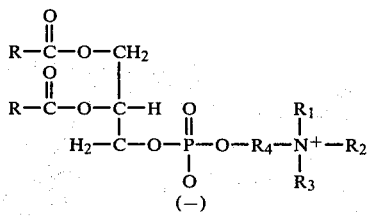

wherein

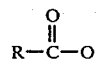

is a long-chain fatty-acid radical; $R_1$, $R_2$ and $R_3$ are alkyl radicals, which alkyl radicals have in total four or more carbon atoms; and $R_4$ is a $C_1$-$C_{10}$ polymethylene radical.

2. The method of claim 1 which includes admixing the water-insoluble compound and the synthetic quaternary-ammonium phosphatidyl compound in the presence of a volatile organic solvent, evaporating the solvent to form a dried mixture, and, thereafter, adding water to the dried mixture, to form a mixed micelle composed of the synthetic phosphatidyl compound and the water-insoluble compound.

3. The method of claim 1 which includes the preparation of an organic solvent solution containing the water-insoluble compound and the phosphatidyl compound, and injecting the solvent solution into water to form a mixed micelle compound, and, thereafter, recovering the mixed micelle compound.

4. The method of claim 1 which includes adding the synthetic quaternary-ammonium phosphatidyl compound to an aqueous suspension of the water-insoluble compound, and, thereafter, homogenizing the mixture to form a mixed micelle compound.

5. The method of claim 3 wherein the organic solvent is selected from the group consisting of methanol, ethanol, dioxane and ether.

6. The method of claim 1 wherein the R is a $C_{14}$–$C_{20}$ fatty-acid radical.

7. The method of claim 1 wherein $R_4$ is a $C_2$–$C_5$ methylene chain, and $R_1$, $R_2$ and $R_3$ are $C_2$–$C_4$ alkyl radicals.

8. The method of claim 1 wherein the synthetic phosphatidyl is selected from the group of:
dioleoyl phosphatidyl-(methylethylene-N-triethyl) ammonium;
dipalmitoyl phosphatidyl-(ethylene-N-dimethylethyl) ammonium;
distearoyl phosphatidyl-(ethylene-N-dimethylethyl) ammonium; and
oleoyl-palmitoyl phosphatidyl-(ethylene-N-dimethylethyl) ammonium.

9. The mixed micelle product produced by the method of claim 8.

10. The mixed micelle product produced by the method of claim 1.

11. The mixed micelle product produced by the method of claim 1, wherein

is a $C_{14}$–$C_{20}$ fatty-acid radical and $R_4$ is trimethylene, and $R_1$ and $R_2$ are methyl radicals and $R_3$ is an ethyl radical.

12. The method of claim 1 wherein

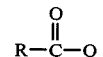

is selected from the group of fatty-acid radicals of oleic, stearic, myristic, palmitic, egg yolk, soybean, linoleic and combinations thereof.

13. The method of claim 1 wherein $R_1$ and $R_2$ are methyl radicals and $R_3$ is an ethyl radical.

14. The method of claim 1 wherein $R_1$, $R_2$ and $R_3$ are the same alkyl radicals.

15. The method of claim 1 wherein $R_4$ is a $C_2$–$C_5$ methylene radical.

* * * * *